United States Patent [19]

Russo

[11] Patent Number: 4,579,555

[45] Date of Patent: Apr. 1, 1986

[54] SURGICAL GRAVITY DRAIN HAVING ALIGNED LONGITUDINALLY EXTENDING CAPILLARY DRAINAGE CHANNELS

[75] Inventor: Ronald D. Russo, Barrington, R.I.

[73] Assignee: SIL-FAB Corporation, Hudson, Mass.

[21] Appl. No.: 557,864

[22] Filed: Dec. 5, 1983

[51] Int. Cl.⁴ .............................................. A61M 27/00
[52] U.S. Cl. ...................................... 604/282; 604/266
[58] Field of Search ................... 609/93, 282, 280, 266

[56] References Cited

U.S. PATENT DOCUMENTS

| | | | |
|---|---|---|---|
| 2,134,152 | 10/1938 | Schwarzmayr | 604/93 |
| 3,860,008 | 1/1975 | Miner et al. | 604/93 |
| 3,957,054 | 5/1976 | McFarlane | 604/282 |
| 4,257,422 | 3/1981 | Duncan | 604/282 X |
| 4,398,910 | 8/1983 | Blake | 604/93 |

FOREIGN PATENT DOCUMENTS 105038  3/1917  United Kingdom ................. 604/93

*Primary Examiner*—Stephen C. Pellegrino
*Attorney, Agent, or Firm*—Weingarten, Schurgin, Gagnebin & Hayes

[57] ABSTRACT

A surgical gravity drain includes biologically inert medical grade silicone rubber extruded to generally parallel longitudinally extending planar surfaces having transversely aligned and longitudinally extending capillary drainage channels. A ribbon of silicone rubber including integrally formed longitudinally extending and laterally spaced ribs defining transversely aligned capillary drainage channels on external ribbon surfaces is disclosed in one embodiment; and a flattened tube of silicone rubber including integrally formed longitudinally extending and laterally spaced ribs defining transversely aligned capillary drainage channels on internal and external tube surfaces is disclosed in a further embodiment. The novel drain of the present invention is substantially clogging-free, collapse-proof, and provides effective long term in situ drainage.

2 Claims, 14 Drawing Figures

SURGICAL GRAVITY DRAIN HAVING ALIGNED LONGITUDINALLY EXTENDING CAPILLARY DRAINAGE CHANNELS

FIELD OF THE INVENTION

This invention is directed the field of surgery, and more particularly, to a novel surgical gravity drain having aligned longitudinally extending capillary drainage channels.

BACKGROUND OF THE INVENTION

In many postoperative medical procedures, it is desirable to drain exudate from various body cavities to further the healing process. A gravity drain typically is inserted into the body of a patient with its internal end in communication with the body cavity to be drained and with its external end connected to a wicking material. Capillary action draws the exudate from the body cavity along the drain and exteriorly of the patient onto the wicking material. Such devices are called upon to provide effective drainage; to prevent tissue to drain adhesion which may induce removal damage; to provide an unobstructed flow path; to provide long term in situ drainage; to readily conform to internal body contours without loss of drainage action; to be comfortable in use; to be capable of expeditious and low-cost manufacture; to be non-inflammatory to surrounding tissue; and to prevent patient trauma. The heretofore known gravity drains are deficient in one or more of these aspects.

SUMMARY OF THE INVENTION

The novel surgical drain of the present invention contemplates an elongated member having longitudinally extending and spaced apart surfaces, and a plurality of longitudinally extending and laterally spaced ribs integrally formed on the surfaces defining a plurality of longitudinally extending capillary drainage channels. In one embodiment, the elongated member includes an elongated ribbon having parallel, generally planar longitudinally extending upper and lower exterior surfaces, and a plurality of longitudinally extending and laterally spaced ribs integrally formed on the longitudinally extending external surfaces defining a plurality of transversely aligned and longitudinally extending capillary drainage channels. In another embodiment, the elongated member includes a flattened elongated tube having spaced apart generally planar longitudinally extending external and interior surfaces, and a plurality of longitudinally extending and laterally spaced ribs integrally formed on the external surfaces and on at least one of the interior surfaces defining a plurality of longitudinally extending and transversely aligned external and internal capillary drainage channels. In both embodiments, the surgical drain of the present invention is extruded from compliant biologically inert silicone rubber that easily conforms to internal body contours without clogging and ensures maximum patient comfort. Th surgical drain of the present invention provides long term in situ drainage, can be manufactured at comparatively low cost, and substantially eliminates removal damage induced by tissue to drain adhesion.

DETAILED DESCRIPTION OF THE DRAWINGS

Other features and advantages of the present invention will become apparent as the invention becomes better understood by referring to the following exemplary and non-limiting detailed description of the preferred embodiments, and to the drawings, wherein.

DETAILED DESCRIPTION OF THE PREFERRED EMBODIMENTS

Figure 1:
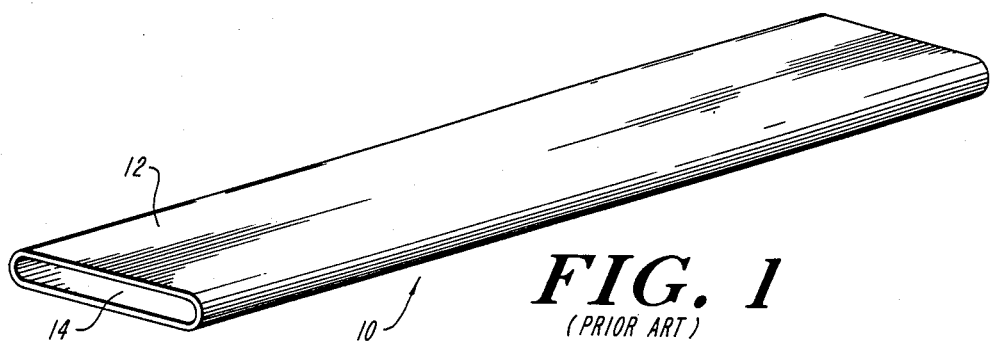
FIG. 1 is a perspective view illustrating a prior art Penrose drain.
Figure 2:
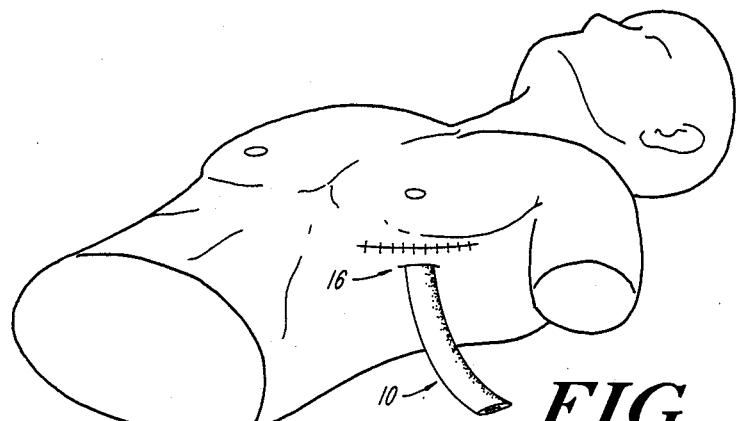
FIG. 2 is a stylized pictorial view illustrating an exemplary use of the prior art Penrose drain.
Figure 3:
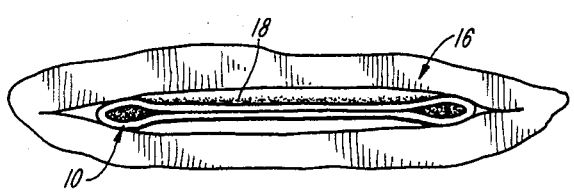
FIG. 3 is a sectional view useful in explaining the operation of the prior art Penrose tube.

Referring now to FIG. 1, generally designated at 10 is a prior art Penrose drain. The drain 10 is a soft and compliant latex rubber tube collapsed on itself having a smooth outer surface 12 and a smooth inner surface 14. The drain 10 is produced by dipping a mandrel, not shown, into latex rubber, in liquid phase. The latex rubber adheres as a thick film to the mandrel, and after curing, the process may be repeated to provide an intended wall thickness. The drain 10 is typically inserted postoperatively into an intended body cavity through an incision generally designated 16 as shown in FIG. 2. Exudate 18 flows from the internal cavity along the external surfaces 12 as well as along the internal surfaces 14 of the Penrose drain 10 by capillary action as illustrated in dark relief in FIG. 3. However, the utility of the drain 10 is limited, among other things, by drainage occlusion produced by tissue pressure induced collapse of the compliant tube; due to tissue to drain adhesion after prolonged use; due to possible patient discomfort and trauma where multiple drains are used to provide an intended drainage capacity; due to the comparatively expensive and time-consuming manufacturing procedure used to fabricate such drains; and due to the possible occlusion of the drain when it is inserted into body contours.

Figure 4:
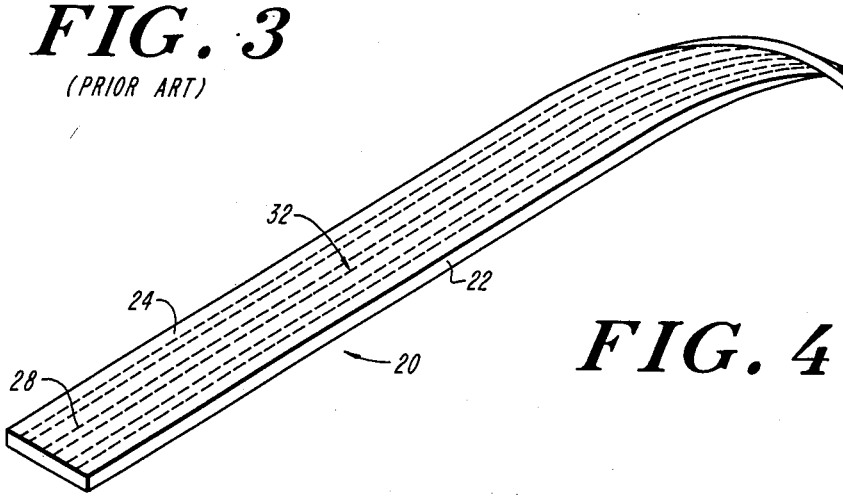
FIG. 4 is a stylized isometric view illustrating one embodiment of the surgical gravity drain having aligned longitudinally extending drainage channels according to the present invention.

Referring now to FIG. 4, generally designated at 20 is a stylized isometric view illustrating one embodiment of the novel surgical gravity drain having aligned longitudinally extending capillary drainage channels according to the present invention. The drain 20 includes an elongated ribbon 22 having an upper generally planar and longitudinally extending external surface 24, and a lower generally planar and longitudinally extending external surface 26. A plurality of longitudinally extending and laterally spaced apart ribs 28 are integrally formed on the surface 24, and a plurality of longitudinally extending and laterally spaced apart ribs 30 are integrally formed on the surface 26. The side walls of adjacent ribs together with the enclosed confronting surface of the surfaces 24, 26 therebetween define a plurality of longitudinally extending and transversely aligned capillary drainage channels generally designated 32, 34 on the surfaces 24, 26. The drain 20 preferably is extruded from medical grade silicone rubber, and a selected amount of X-ray opaque barium can be incorporated into the silicone rubber prior to extrusion to provide X-ray observability.

Figure 5A:
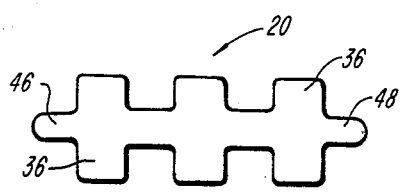
FIGS. 5A–5B are sectional views illustrating four exemplary configurations of the embodiment of FIG. 4.
Figure 5B:
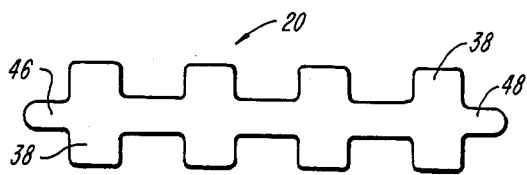
Figure 5C:
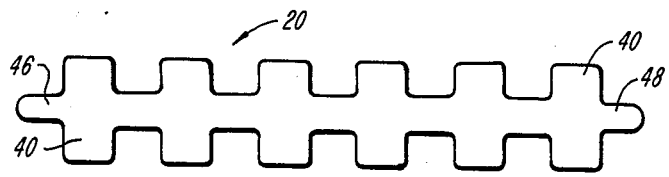
Figure 5D:
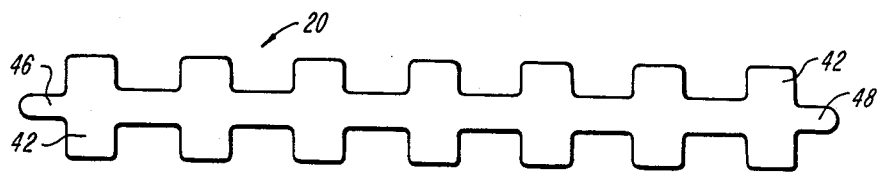

The particular number of longitudinally extending ribs on a particular gravity drain is selected in accordance with a desired drainage capability. Referring now to FIG. 5, three longitudinally extending laterally spaced and transversely aligned ribs 36 are illustrated in FIG. 5A; four longitudinally extending laterally spaced and transversely aligned ribs 38 are illustrated in FIG. 5B; six longitudinally extending laterally spaced and transversely aligned ribs 40 are illustrated in FIG. 5C; and seven longitudinally extending laterally spaced and transversely aligned ribs 42 are illustrated in FIG. 5D. In each of the configurations shown in FIGS. 5A–5D, the ribs preferably have a U-shaped cross-section that defines a deep capillary drainage channel between adjacent ribs, although, as will be appreciated by those skilled in the art, other suitable cross-sections can be employed as well without departing from the inventive concept. The transverse alignment of the ribs 36, 38, 40, 42 on the upper and lower surfaces of the drain provides structural support thereto that substantially eliminates channel occlusions due to tissue pressure and due to bights formed in the drain when inserted into body contours.

Figure 6:
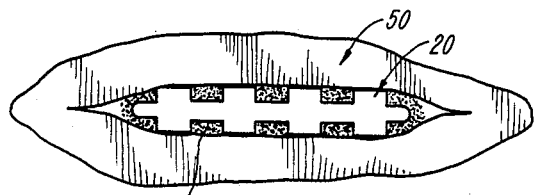
FIG. 6 is a sectional view useful in explaining the operation of the embodiment of FIG. 4.

Longitudinally extending and laterally directed flanges 46, 48 are preferably integrally formed at the sides of the drain as illustrated in FIG. 5. The drain 20 is typically inserted into an intended body cavity through a stab wound generally designated 50, and exudate 52 is guided by capillary action both in the longitudinally extending and transversely aligned capillary drainage channels defined between adjacent ribs and between the channels defined between the outside longitudinally extending edges of the outermost ribs and corresponding ones of the longitudinally extending and laterally directed flanges as illustrated in dark relief in FIG. 6. The novel surgical gravity drain of the present invention has been found to provide enhanced drainage, clogging-free operation and comfortable long term in situ use without inducing patient trauma.

Figure 7:
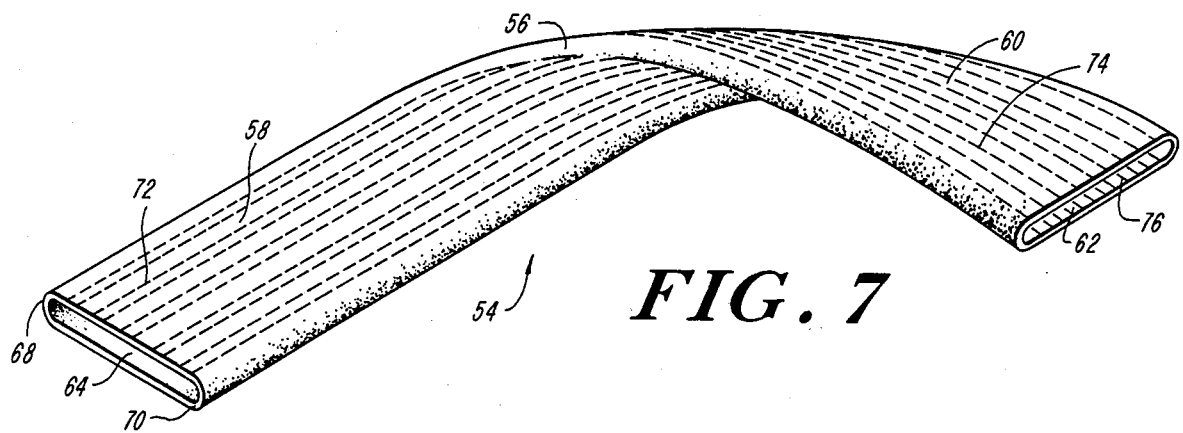
FIG. 7 is a stylized isometric view illustrating another embodiment of the surgical gravity drain having aligned longitudinally extending drainage channels according to the present invention.

Referring now to FIG. 7, generally designated at 54 is a stylized isometric view illustrating embodiment of the gravity drain having aligned longitudinally extending capillary drainage channels according to the present invention. The drain 54 includes a flattened, elongated length of extruded medical-grade silicone rubber tube 56 having an upper generally planar and longitudinally extending external surface 58, a lower generally planar and longitudinally extending external surface 60, and upper and lower generally planar and longitudinally extending interior surfaces 62, 64. Arcuate side wall 68, 70 join the surfaces 58, 60 and 62, 64 longitudinally along respective sides thereof. A plurality of longitudinally extending and laterally spaced ribs 72 are integrally formed on the top surface 58. A plurality of longitudinally extending laterally spaced and transversely aligned ribs 74 are integrally formed on the bottom surface 60, and a plurality of longitudinally extending laterally spaced and transversely aligned ribs 76 are integrally formed on the interior surface 62. The ribs 72, 74, 76 are preferably extruded during formation of the drain 54.

Figure 8A:
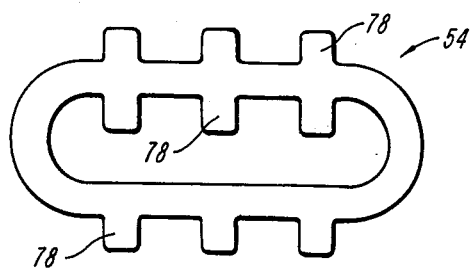
FIGS. 8A–8C are sectional views illustrating three exemplary configurations of the embodiment of FIG. 7.
Figure 8B:
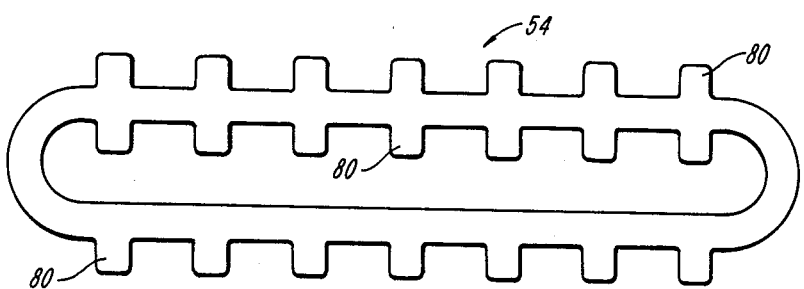
Figure 8C:
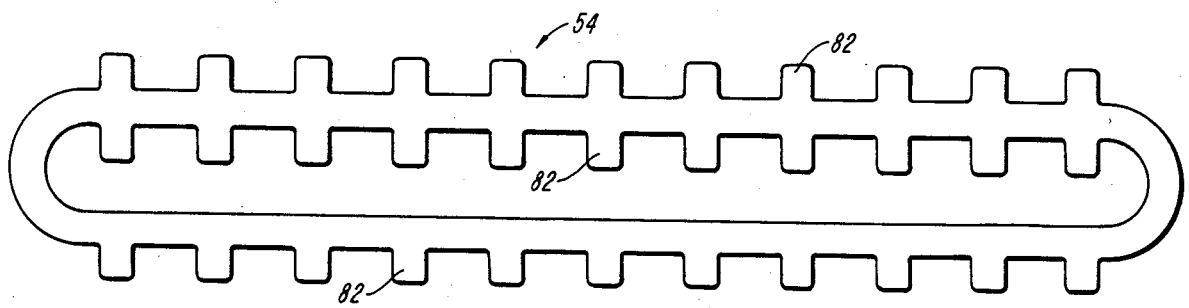

The particular number of longitudinally extending ribs on a particular gravity drain is selected in accordance with a desired drainage capability. Referring now to FIG. 8, three rows of longitudinally extending laterally spaced and transversely aligned ribs 78 are illustrated in FIG. 8A; seven rows of longitudinally extending laterally spaced and transversely aligned ribs 80 are illustrated in FIG. 8B; and eleven rows of longitudinally extending laterally spaced and transversely aligned ribs 82 are illustrated in FIG. 8C. The ribs 78, 80, 82 each preferably have a U-shaped cross-section that defines a deep capillary drainage channel between adjacent ribs. It will be appreciated that the ribs can have other cross-sections as well without departing from the inventive concept. Additional longitudinally extending laterally spaced and transversely aligned ribs, not illustrated, can be integrally formed on the other interior surface of the drain without departing from the inventive concept. The transverse alignment of the ribs 78, 80, 82 provides structural support to the drain that substantially eliminates channel occlusion due to tissue pressure, due to bights formed in the drain when inserted into body contours, and due to tube collapse.

Figure 9:
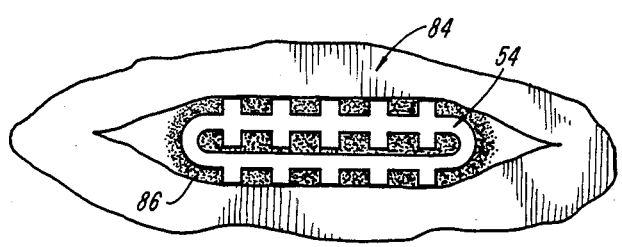
FIG. 9 is a sectional view useful in explaining the operation of the embodiment of FIG. 7.

The drain 54 is typically inserted through a stab wound generally designated 84 provided therefor and into the internal cavity to be drained, and exudate 86 is guided by capillary action in the longitudinally extending channels defined between adjacent external ribs, in the longitudinally extending channels defined between adjacent internal ribs, as well as along the sides of the drain as illustrated in dark relief in FIG. 9. The novel surgical gravity drain of the present invention has been found to provide enhanced drainage, clogging free operation, and long term in situ use without inducing patient trauma.

It will be appreciated that many modifications of the presently disclosed invention are possible without departing from the scope of the appended claims.

What is claimed is:

1. A surgical gravity drain, comprising:
   an elongated tubular member of a compliant, flexible, and biologically inert material having first and second generally parallel and longitudinally extending external planar surfaces and at least one generally parallel and longitudinally extending third interior surface adjacent one of said first and said second external surfaces;
   a plurality of longitudinally extending and laterally spaced first ribs integrally formed on said first planar surface of said elongated member defining a plurality of longitudinally extending exudate receiving channels between adjacent first ribs and corresponding included portions of said first external surface;
   a plurality of longitudinally extending and laterally spaced second ribs integrally formed on said second planar surface of said elongated member defining a plurality of longitudinally extending exudate receiving channels between adjacent second ribs and corresponding included portions of said second external surface;
   a plurality of longitudinally extending and laterally spaced third ribs integrally formed on said third planar surface of said elongated member defining a plurality of longitudinally extending exudate receiving channels between adjacent third ribs and corresponding included portions of said third internal surface;

individual ones of said third ribs on said third internal surface being integrally formed with said member such that they are transversely aligned with corresponding ones of said ribs integrally formed on said at least one of said first and said second external surfaces and cooperative therewith to act as support columns that provide structural strength to said drain.

2. The invention of claim 1 wherein said drain is an extruded length of medical-grade silicone rubber.

* * * * *